(12) United States Patent
Jonassen et al.

(10) Patent No.: US 7,595,172 B2
(45) Date of Patent: *Sep. 29, 2009

(54) METHOD FOR MAKING ACYLATED POLYPEPTIDES

(75) Inventors: Ib Jonassen, Valby (DK); Michi Egel-Mitani, Vedbaek (DK); Per Balschmidt, Espergaerde (DK); Jan Markussen, Herlev (DK); Ivan Diers, Vaerlose (DK); Thomas Borglum Kjeldsen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 679 days.

This patent is subject to a terminal disclaimer.

(21) Appl. No.: 10/205,110

(22) Filed: Jul. 24, 2002

(65) Prior Publication Data

US 2003/0144471 A1   Jul. 31, 2003

Related U.S. Application Data

(60) Provisional application No. 60/310,793, filed on Aug. 8, 2001.

(30) Foreign Application Priority Data

Jul. 24, 2001   (DK) ............................... 2001 01141

(51) Int. Cl.
   *A61K 38/00*   (2006.01)
(52) U.S. Cl. ...................................... 435/69.1; 530/300
(58) Field of Classification Search ........................ None
   See application file for complete search history.

(56) References Cited

U.S. PATENT DOCUMENTS

| | | | |
|---|---|---|---|
| 5,252,466 A | 10/1993 | Cronan, Jr. ................ 435/69.7 |
| 5,316,923 A | 5/1994 | Christiansen ............... 435/69.9 |
| 5,395,922 A | 3/1995 | Bjorn et al. | |
| 5,646,242 A | 7/1997 | Baker et al. ................. 530/303 |
| 5,750,497 A | 5/1998 | Havelund et al. | |
| 5,905,140 A | 5/1999 | Hansen ....................... 530/303 |
| 6,011,007 A | 1/2000 | Havelund et al. ............... 514/3 |
| 6,110,703 A | 8/2000 | Egel-Mitani et al. | |
| 6,500,645 B1 | 12/2002 | Kjeldsen et al. | |
| 2003/0082671 A1* | 5/2003 | Hoeg-Jensen et al. ...... 435/68.1 |
| 2005/0272125 A1* | 12/2005 | Hoeg-Jensen et al. ...... 435/69.1 |

FOREIGN PATENT DOCUMENTS

| | | |
|---|---|---|
| EP | 0712862 A2 | 5/1996 |
| EP | 1132404 | 9/2001 |
| JP | 4-504846 | 8/1992 |
| JP | 10-501695 | 2/1998 |
| JP | 2000-60556 | 2/2000 |
| JP | 2000-513941 | 8/2000 |
| JP | 2001-507574 | 6/2001 |
| JP | 2000-501617 | 12/2002 |
| JP | 9-502867 | 3/2007 |
| WO | WO 98/08871 | 3/1998 |
| WO | WO 98/08872 | 3/1998 |
| WO | WO 98/28429 | 7/1998 |
| WO | WO 00/55119 | 9/2000 |

* cited by examiner

*Primary Examiner*—Christopher R. Tate
*Assistant Examiner*—Roy Teller
(74) *Attorney, Agent, or Firm*—Shelby J. Walker

(57) ABSTRACT

The present invention related to a method of producing polypeptides in transformed host cells by expressing a precursor molecule of the desired polypeptide which are to be acylated in a subsequent in vitro step. The invention is also related to DNA-sequences, vectors and transformed host cells for use in the claimed method. Further, the present invention is related to certain precursors of the desired polypeptides and certain acylation methods. The invention provides a method for making polypeptides being preferentially acylated in certain lysine $\epsilon$-amino groups.

24 Claims, 1 Drawing Sheet

SEQUENCE LISTING

<160> NUMBER OF SEQ ID NOS: 51

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Glu Glu Ala His Lys
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Glu Glu Ala Glu Ala His Lys
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Glu Glu Ala Glu Ala Glu Ala His Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic

<400> SEQUENCE: 4

Glu Glu Gly His Lys
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic

<400> SEQUENCE: 5

Glu His Pro Lys
1

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

```
Glu Glu Gly Glu Pro Lys
 1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Glu Glu His Cys Lys
 1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic

<400> SEQUENCE: 8

Glu Glu His His Lys
 1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Glu His His His Lys
 1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic

<400> SEQUENCE: 10

Glu His Ala His Lys
 1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic

<400> SEQUENCE: 11

Glu Gly Ala His Lys
 1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Glu His Gly His Gly Lys
```

```
                     1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

Glu Glu Ala His Glu Leu Lys
 1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

Glu Glu Ala His Glu Ile Lys
 1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

Glu Glu Ala His Glu Val Lys
 1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

Glu Glu Ala His Glu Met Lys
 1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Glu Glu Ala His Glu Phe Lys
 1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic

<400> SEQUENCE: 18

Glu Glu Ala His Glu Tyr Lys
 1               5
```

```
<210> SEQ ID NO 19
<211> LENGTH: 7
<212> TYPE: PRT
<213> ORGANISM: Artificial Sequence
<220> FEATURE:
<223> OTHER INFORMATION: Synthetic

<400> SEQUENCE: 19

Glu Glu Ala His Glu Trp Lys
 1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Glu Glu Gly Asn Thr Thr Pro Lys
 1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Glu Glu Gly Asn Glu Thr Glu Pro Lys
 1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic

<400> SEQUENCE: 22

Glu Glu Gly Asn Asp Thr Glu Pro Lys
 1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic

<400> SEQUENCE: 23

Glu Glu Gly Asn Thr Thr Glu Pro Lys
 1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic

<400> SEQUENCE: 24

Gln Asp Ala His Lys
 1               5
```

```
<210> SEQ ID NO 25
<211> LENGTH: 5
<212> TYPE: PRT
<213> ORGANISM: Artificial Sequence
<220> FEATURE:
<223> OTHER INFORMATION: Synthetic

<400> SEQUENCE: 25

Gln Asp Thr Ala Lys
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic

<400> SEQUENCE: 26

Asp Asp Asp Asp Lys
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic

<400> SEQUENCE: 27

Glu Ala Glu Ala Trp His Trp Leu Lys
1               5

<210> SEQ ID NO 28
<211> LENGTH: 11
<212> TYPE: PRT
<213> ORGANISM: Artificial Sequence
<220> FEATURE:
<223> OTHER INFORMATION: Synthetic

<400> SEQUENCE: 28

Glu Ala Glu Ala Glu Ala Trp His Trp Leu Lys
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic

<400> SEQUENCE: 29

Glu Glu Ala Glu Ala Trp His Trp Leu Lys
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

Glu Glu Glu Ala Trp His Trp Leu Lys
1               5
```

```
<210> SEQ ID NO 31
<211> LENGTH: 9
<212> TYPE: PRT
<213> ORGANISM: Artificial Sequence
<220> FEATURE:
<223> OTHER INFORMATION: Synthetic

<400> SEQUENCE: 31

Leu Asp Gly Arg Leu Glu Ala Leu Lys
 1               5

<210> SEQ ID NO 32
<211> LENGTH: 11
<212> TYPE: PRT
<213> ORGANISM: Artificial Sequence
<220> FEATURE:
<223> OTHER INFORMATION: Synthetic

<400> SEQUENCE: 32

Glu Glu Leu Asp Gly Arg Leu Glu Ala Leu Lys
 1               5                  10

<210> SEQ ID NO 33
<211> LENGTH: 11
<212> TYPE: PRT
<213> ORGANISM: Artificial Sequence
<220> FEATURE:
<223> OTHER INFORMATION: Synthetic

<400> SEQUENCE: 33

Glu Glu Leu Asp Ala Arg Leu Glu Ala Leu Lys
 1               5                  10

<210> SEQ ID NO 34
<211> LENGTH: 4
<212> TYPE: PRT
<213> ORGANISM: Artificial Sequence
<220> FEATURE:
<223> OTHER INFORMATION: Synthetic

<400> SEQUENCE: 34

Asp Thr His Lys
 1

<210> SEQ ID NO 35
<211> LENGTH: 4
<212> TYPE: PRT
<213> ORGANISM: Artificial Sequence
<220> FEATURE:
<223> OTHER INFORMATION: Synthetic

<400> SEQUENCE: 35

Asp Ala His Lys
 1

<210> SEQ ID NO 36
<211> LENGTH: 7
<212> TYPE: PRT
<213> ORGANISM: Artificial Sequence
<220> FEATURE:
<223> OTHER INFORMATION: Synthetic

<400> SEQUENCE: 36

Glu His His Gly His Gly Lys
 1               5

<210> SEQ ID NO 37
```

```
<210> SEQ ID NO 37
<211> LENGTH: 4
<212> TYPE: PRT
<213> ORGANISM: Artificial Sequence
<220> FEATURE:
<223> OTHER INFORMATION: Synthetic

<400> SEQUENCE: 37

Asp Ser His Lys
 1

<210> SEQ ID NO 38
<211> LENGTH: 5
<212> TYPE: PRT
<213> ORGANISM: Artificial Sequence
<220> FEATURE:
<223> OTHER INFORMATION: Synthetic

<400> SEQUENCE: 38

Gln Asp Thr His Lys
 1               5

<210> SEQ ID NO 39
<211> LENGTH: 11
<212> TYPE: PRT
<213> ORGANISM: Artificial Sequence
<220> FEATURE:
<223> OTHER INFORMATION: Synthetic

<400> SEQUENCE: 39

Glu Ala Glu Ala Glu Ala Gln Asp Thr His Lys
 1               5                  10

<210> SEQ ID NO 40
<211> LENGTH: 9
<212> TYPE: PRT
<213> ORGANISM: Artificial Sequence
<220> FEATURE:
<223> OTHER INFORMATION: Synthetic

<400> SEQUENCE: 40

Glu Ala Glu Ala Gln Asp Thr His Lys
 1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic

<400> SEQUENCE: 41

Glu Ala Gln Asp Thr His Lys
 1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic

<400> SEQUENCE: 42

Trp His Trp Leu Lys
 1               5

<210> SEQ ID NO 43
<211> LENGTH: 7
```

```
<212> TYPE: PRT
<213> ORGANISM: Artificial Sequence
<220> FEATURE:
<223> OTHER INFORMATION: Synthetic

<400> SEQUENCE: 43

Glu Glu Trp His Trp Leu Lys
1               5

<210> SEQ ID NO 44
<211> LENGTH: 11
<212> TYPE: PRT
<213> ORGANISM: Artificial Sequence
<220> FEATURE:
<223> OTHER INFORMATION: Synthetic

<400> SEQUENCE: 44

Glu Glu Glu Ala Glu Ala Trp His Trp Leu Lys
1               5                   10

<210> SEQ ID NO 45
<211> LENGTH: 5
<212> TYPE: PRT
<213> ORGANISM: Artificial Sequence
<220> FEATURE:
<223> OTHER INFORMATION: Synthetic

<400> SEQUENCE: 45

Glu Glu Ala Glu Lys
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic

<400> SEQUENCE: 46

Glu Glu Gly Glu Pro Lys
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic

<400> SEQUENCE: 47

Glu Ala Gln Asp Ala His Lys
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Glu Ala Glu Ala Gln Asp Ala His Lys
1               5

<210> SEQ ID NO 49
<211> LENGTH: 11
<212> TYPE: PRT
```

-continued

```
<213> ORGANISM: Artificial Sequence
<220> FEATURE:
<223> OTHER INFORMATION: Synthetic

<400> SEQUENCE: 49

Glu Ala Glu Ala Glu Ala Gln Asp Ala His Lys
 1               5                  10

<210> SEQ ID NO 50
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)...(4)
<223> OTHER INFORMATION: Xaa = Ala, Thr or Ser

<400> SEQUENCE: 50

Asp Xaa His Lys
 1

<210> SEQ ID NO 51
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)...(2)
<223> OTHER INFORMATION: Xaa = Glu, Asp, Asn, Glu, Thr, Gly, Leu, Ile,
      Val, Met, Phe or Tyr
<220> FEATURE:
<221> NAME/KEY: PEPTIDE
<222> LOCATION: (2)...(3)
<223> OTHER INFORMATION: Xaa = Leu, Ile, Val, Met, Phe, Tyr, Trp or Cys

<400> SEQUENCE: 51

His Xaa Xaa Lys
 1
```

METHOD FOR MAKING ACYLATED POLYPEPTIDES

CROSS REFERENCE TO RELATED APPLICATIONS

This application claims priority under 35 U.S.C. 119 of Danish application no. PA 2001 01141 filed on Jul. 24, 2001, and U.S. application No. 60/310,793 filed on Aug. 8, 2001, the contents of which are fully incorporated herein by reference.

FIELD OF THE INVENTION

The present invention is related to a method of producing polypeptides in transformed host cells by expressing a precursor molecule of the desired polypeptide which is to be acylated and subsequently cleaved at a Lys cleavage site in a subsequent in vitro step. The invention is also related to DNA-sequences, vectors and transformed host cells for use in the claimed method. Further, the present invention is related to certain precursors of the desired polypeptides and certain acylation methods.

BACKGROUND OF THE INVENTION

Recombinant DNA technology has enabled expression of foreign (heterologous) polypeptides in microbial and other host cells. In yeast expression of heterologous polypeptides after transformation of yeast cells with suitable expression vectors comprising DNA sequences coding for said polypeptides has been successful for many species of polypeptides, such as insulin and insulin precursors, glucagon, glucagon like peptides and analogues thereof.

A common problem with expression of proteins or polypeptides of a limited size in a recombinant host is, however, proteolytic degradation of the expressed product by proteolytic enzymes produced by the host organism.

Thus, the isolated product may be a heterogeneous mixture of species of the desired polypeptide having different amino acid chain lengths. Another problem encountered in production of heterologous polypeptides in yeast may be low yield, presumably due to proteolytic processing both in intracellular compartments and at the plasma membrane caused by aberrant processing at internal sites in the polypeptide. Yeast contains a number of proteases used for processing yeast proteins e.g. Kex2p and Yps1p which cleave at the C-terminal side of a dibasic amino acid sequence, and the carboxypeptidase Kex1p which digests remaining basic amino acids after the endoproteolytic digestion by Kex2p, and Ste13p or Dap2p which cleave at X-Ala or X-Pro.

Some polypeptides, e.g. polypeptides having from about 10 to about 100 amino acids chains and none or a few disulphide bonds and/or are rich in basic amino acids, such as β-endorphine, glucagon and glucagon like peptides may be especially susceptible to intracellular and extracellular proteolytic degradation when expressed in a transformed host cell due to their short-chain open and non-disulfide stabilized structure resulting in an inhomogeneous product which may be proteolytically degraded in the N- and C-terminal ends as well as endoproteolytically degraded.

Furthermore, N-terminal cleavage of expressed polypeptides by host cell produced enzymes may cause decreased yield of a desired product with correct N-terminal if the N-terminal of the expressed product constitutes a cleavage site for endogenous enzymes. In yeast for example the enzyme Ste13p cleaves at X-Ala or X-Pro, where X can be any amino acid residue. Thus, polypeptides with an Ala or Pro residue as the second residue from the N-terminal end may be cleaved at the N-terminal end and the recovered polypeptide may be a mixture of different degradation products complicating the recovery process and reducing the overall yield.

Furthermore, small polypeptides with no or little tertiary structure and low content of α-helices may have a higher tendency to form β-sheets that stack on each other and form fibrils during fermentation and down stream separation and purification steps in large scale production. Formation of fibrils may cause unwanted precipitation with loss of the desired product. Fibrillation may be prevented by treatment at high pH. However, such alkaline treatment is pretty harsh to the product and may cause unwanted formation of D-amino acids residues.

Human GLP-1 is a 37 amino acid residue peptide originating from preproglucagon which is synthesised in the L-cells in the distal ileum, in the pancreas and in the brain. Processing of preproglucagon to give GLP-1$_{(7-36)}$amide, GLP-1$_{(7-37)}$ and GLP-2 occurs mainly in the L-cells. Both GLP-1 and GLP-2 has an Ala as the second amino acid residue from the N-terminal end and are thus prone for N-terminal cleavage when expressed in a host organism such as yeast.

Introduction of lipophilic acyl groups in naturally occurring peptides or analogues thereof has shown to lead to acylated peptides which have a protracted profile relative to the native peptide or unmodified analogues. This phenomenon is disclosed and demonstrated in WO 98/08871 which discloses acylation of GLP-1 and analogues thereof and in WO 98/08872 which discloses acylation of GLP-2 and analogues thereof.

When acylating precursor molecules comprising a Lys cleavage site acylation of the Lys cleavage site should be avoided as such acylation will prevent the subsequent cleavage. The method according to the present invention is a solution to this problem as it will appear from the following.

SUMMARY OF THE INVENTION

In its broadest aspect, the present invention is related to a method of producing polypeptides in transformed host cells by expressing a precursor molecule of the desired polypeptide said precursor molecule comprising an N-terminal extension which allows for preferential acylation of the expressed precursor molecule and protects the expressed precursor molecule against proteolytic degradation within the host cell or in the culture medium. In addition, the precursor molecule is easier to purify and has a less tendency to form fibrils thus allowing more flexibility when selecting down stream separation and purification steps in large scale operations.

In one aspect the present invention is related to a method for making a polypeptide comprising at least one lysine residue being acylated in its ε-amino group, said method comprising the following steps:

(i) culturing a host cell comprising a polynucleotide sequence encoding a precursor molecule of the desired polypeptide under suitable conditions for expression of said precursor molecule, the precursor molecule comprising the desired polypeptide and an N-terminal extension, said N-terminal extension being cleavable from the desired polypeptide at a lysine cleavage site;

(ii) separating the expressed precursor molecule from the culture broth;

(iii) preferentially acylating the ε-amino group of at least one lysine in the desired polypeptide without acylating the ε-amino group of the Lys-cleavage site in the N-terminal extension;

(iv) removing the N-terminal extension from the acylated precursor molecule by enzymatic cleavage and
(v) isolating the acylated polypeptide by suitable means.

DETAILED DESCRIPTION OF THE INVENTION

The N-terminal extension will typically be up to 15 amino acids in length and may be from 3-15; 3-12; 3-10; 3-9; 3-8; 3-7; 3-6; or 3-5 amino acids in length. The amino acids in the N-terminal extension are selected with a multiple purpose: 1) to prevent or minimize acylation of the Lys cleavage site at the C-terminal end of the N-terminal extension; 2) to protect the expressed precursor molecule against endoproteolytic degradation; and 3) to prevent precipitation caused by fibrillation during fermentation and down stream processing steps such as separation and purification in large scale production. Furthermore, the amino acid residues at both ends of the N-terminal extension should be selected so as to ensure efficient cleavage of the N-terminal extension from the desired polypeptide at the C-terminal end (at the Lys-cleavage site) and in the yeast cell at the N-terminal end from possible upstream sequences such as pre- or pre-pro peptides which have the purpose of ensuring transport of the expressed polypeptide out of the host cell and into the culture medium. Finally, the N-terminal extension may serve as a tag for purification purposes.

In one embodiment the present invention is related to a method, wherein one or more amino acid residues in the N-terminal extension are capable of establishing a metal ion complex binding site together with one or more amino acid residues in the N-terminal end of the polypeptide.

The N-terminal extension comprising a metal ion binding site may be derived from the N-terminal of albumins. Examples of $Cu^{+2}$ binding sites are the N-terminals of bovine (Asp-Thr-His-Lys, SEQ ID NO:34) and human (Asp-Ala-His-Lys, SEQ ID NO:35) serum albumin (Peters, T.; All about Albumin, Academic Press, USA (1996) p 121-123) which could be used as the N-terminal extension in synergy with heavy metal ions such as $Cu^{++}$ present in the culture medium and during the acylation step (iii).

The N-terminal extension comprising a metal ion binding site may also be derived from the Zn-binding sites in especially some of the metalloendopeptidases EC 3.4.24-.

In one embodiment, the N-terminal extension comprises at least one histidine residue. The histidine residues in the N-terminal extension are typically positioned 1-4 residues from the lysine cleavage site.

Examples of N-terminal extensions comprising at least one histidine residue are Glu-Glu-Ala-His-Lys (SEQ ID NO:1); Glu-(Glu-Ala)$_2$-His-Lys (SEQ ID NO:2); Glu-(Glu-Ala)$_3$His-Lys (SEQ ID NO:3); Glu-Glu-Gly-His-Lys (SEQ ID NO:4); Glu-His-Pro-Lys (SEQ ID NO:5); Glu-Glu-Gly-Glu-Pro-Lys (SEQ ID NO:6); Glu-Glu-His-Cys-Lys (SEQ ID NO:7); Glu-Glu-His-His-Lys (SEQ ID NO:8); Glu-His-His-His-Lys (SEQ ID NO:9); Glu-His-Ala-His-Lys (SEQ ID NO:10); Glu-Gly-Ala-His-Lys (SEQ ID NO:11); Glu-His-Gly-His-Gly-Lys (SEQ ID NO:12); Glu-Glu-Ala-His-Glu-Leu-Lys (SEQ ID NO:13); Glu-Glu-Ala-His-Glu-Ile-Lys (SEQ ID NO:14); Glu-Glu-Ala-His-Glu-Val-Lys (SEQ ID NO:15); Glu-Glu-Ala-His-Glu-Met-Lys (SEQ ID NO:16); Glu-Glu-Ala-His-Glu-Phe-Lys (SEQ ID NO:17); Glu-Glu-Ala-His-Glu-Tyr-Lys (SEQ ID NO:18); Glu-Glu-Ala-His-Glu-Trp-Lys (SEQ ID NO:19); Gln-Asp-Ala-His-Lys (SEQ ID NO:24); Glu-Glu-Glu-Ala-Trp-His-Trp-Leu-Lys (SEQ ID NO:30); Asp-Thr-His-Lys (SEQ ID NO:34); Glu-His-His-Gly-His-Gly-Lys (SEQ ID NO:36); Asp-Ser-His-Lys (SEQ ID NO:37); Gln-Asp-Thr-His-Lys (SEQ ID NO:38); Glu-Ala-Glu-Ala-Glu-Ala-Gln-Asp-Thr-His-Lys (SEQ ID NO:39); Glu-Ala-Glu-Ala-Gln-Asp-Thr-His-Lys (SEQ ID NO:40); Glu-Ala-Gln-Asp-Thr-His-Lys (SEQ ID NO:41); Trp-His-Trp-Leu-Lys (SEQ ID NO:42); Glu-Glu-Trp-His-Trp-Leu-Lys (SEQ ID NO:43); Glu-Glu-Glu-Ala-Glu-Ala-Trp-His-Trp-Leu-Lys (SEQ ID NO:44); Glu-Ala-Gln-Asp-Ala-His-Lys (SEQ ID NO:47); Glu-Ala-Glu-Ala-Gln-Asp-Ala-His-Lys (SEQ ID NO:48); and Glu-Ala-Glu-Ala-Glu-Ala-Gln-Asp-Ala-His-Lys (SEQ ID NO:49).

In another embodiment the present invention is related to a method, wherein the N-terminal extension of the precursor molecule comprises at least one amino acid residue that is capable of establishing a salt bridge (ion bond) with the lysine cleavage site N-terminal to the polypeptide.

In this embodiment, the N-terminal extension will typically comprise at least one Glu or Asp which may be positioned between 1 to 5 residues from the lysine cleavage site. In one such embodiment, the N-terminal extension comprises a Glu-Glu-sequence. Examples of N-terminal extensions comprising a Glu residue are Glu-Glu-Ala-Glu-Lys (SEQ ID NO:45); Glu-Glu-Gly-Glu-Pro-Lys (SEQ ID NO:46) and Glu-Glu-Lys. In this embodiment, the N-terminal extension may furthermore be capable of forming an α-helix.

N-terminal extensions functioning both as a tag and being capable of forming a salt bridge are sequences derived from the enterokinase site in bovine trypsinogen that is known to bind $Ca^{+2}$. Thus a suitable N-terminal extension for use in the present process is Asp-Asp-Asp-Asp-Lys (SEQ ID NO:26).

An N-terminal extension which is capable of forming an α-helix will typically comprise a sequence that contains alternating polar and non-polar amino acids as described by Zhu et al, Protein Science 2, 384-394 (1993). Examples of such sequences are Glu-Glu-Ala-Glu-Ala-Trp-His-Trp-Leu-Lys (SEQ ID NO:29), Glu-Glu-Glu-Ala-Trp-His-Trp-Leu-Lys (SEQ ID NO:30); Leu-Asp-Gly-Arg-Leu-Glu-Ala-Leu-Lys (SEQ ID NO:31); Glu-Glu-Leu-Asp-Gly-Arg-Leu-Glu-Ala-Leu-Lys (SEQ ID NO:32); Glu-Glu-Leu-Asp-Ala-Arg-Leu-Glu-Ala-Leu-Lys (SEQ ID NO:33); Glu-Glu-Trp-His-Trp-Leu-Lys (SEQ ID NO:43); and Glu-Glu-Glu-Ala-Glu-Ala-Trp-His-Trp-Leu-Lys (SEQ ID NO:44).

In this embodiment, the N-terminal extension may also comprise a eukaryotic N-glycosylation site N-X-S or N-X-T where X can be any amino acid residue except Pro. Examples of N-terminal extensions comprising a glycosylation site are Glu-Glu-Gly-Asn-Thr-Thr-Pro-Lys (SEQ ID NO:20), Glu-Glu-Gly-Asn-Glu-Thr-Glu-Pro-Lys (SEQ ID NO:21), Glu-Glu-Gly-Asn-Asp-Thr-Glu-Pro-Lys (SEQ ID NO:22) and Glu-Glu-Gly-Asn-Thr-Thr-Glu-Pro-Lys (SEQ ID NO: 23).

In a further embodiment the present invention is related to a method, wherein the desired polypeptide is sensitive to proteolytic degradation at its N-terminal end and wherein the N-terminal extension prevents or minimizes such proteolytic degradation. Such polypeptides may be characterized by having an Ala, Ser, Pro or Gly residue as the second amino acid residue from the N-terminal end.

In a still further embodiment the polypeptide has a His or Tyr as the N-terminal amino acid residue.

In a more specific embodiment, the N-terminal extension has the formula $X_n$------$X_1$-Lys wherein Lys is a cleavage site and $X_n$------$X_1$ is a peptide sequence of from 2-14 amino acid residues in length having the function of preventing or minimizing that the free ε-amino group in the Lys cleavage site will be acylated in the above described step (iii). $X_n$------$X_1$ will furthermore protect the expressed desired polypeptide from endoproteolytic cleavage and will prevent precipitation caused by fibrillation of the N-terminal extended molecule during fermentation and down stream separation and purification steps. The amino acid residues in $X_n$------$X_1$ are furthermore selected so that optimal cleavage of the N-terminal extension at its C-terminal end (at Lys) is achieved. Furthermore, the amino acid residues in the N-terminal end of the extension are chosen so that cleavage is optimized in the yeast cell from upstream signal-leader-sequences at a KEX cleavage site (Lys,Arg). The amino acid residues in $X_n$------$X_1$ may in principle be any amino acid residue except Lys as long as the peptide sequence fulfils at least one of the required purposes with the proviso that at least one X is His or Glu or Asp and that number two amino acid residue from the N-terminal end of the extension is preferably not Ala or Pro.

In one embodiment $X_n$------$X_1$ is of 2-12 amino acid residues in length. In another embodiment $X_n$------$X_1$ is of 2-10; 2-9; 2-8; 2-7; 2-6; or 2-5 amino acid residues in length.

In another embodiment $X_n$------$X_1$ contains 2-8 amino acid residues which are selected from the group consisting of His; Glu; Ala; Asp; Gly; and Pro.

In another embodiment $X_n$------$X_1$ contains 4-10 amino acid residues which are selected from the group consisting of Glu; Asp; Ala; His; Trp; Tyr; Ile; Val; Met; and Phe.

In a further embodiment $X_n$------$X_1$ contains 5-8 amino acid residues selected from the group consisting of Glu; Asp; Gly; Asn; Thr; Ser; and Pro.

In all embodiments Glu and/or Asp are preferably selected as the first and second amino acid residue from the N-terminal end of the extension to ensure proper cleavage at this end from an upstream pre- or pre-pro-sequence by means of a Kex2p cleavage site. Furthermore, one or more Glu and/Asp residues at the N-terminal end of the N-terminal extension will protect the N-terminal end of the ultimately desired polypeptide from in vivo degradation during fermentation.

Examples of $X_n$------$X_1$-Lys sequences are Glu-Glu-Ala-His-Lys (SEQ ID NO:1); Glu-(Glu-Ala)$_2$-His-Lys (SEQ ID NO:2); Glu-(Glu-Ala)$_3$His-Lys (SEQ ID NO:3); Glu-Glu-Gly-His-Lys (SEQ ID NO:4); Glu-His-Pro-Lys (SEQ ID NO:5); Glu-Glu-Gly-Glu-Pro-Lys (SEQ ID NO:6); Glu-Glu-His-Cys-Lys (SEQ ID NO:7); Glu-Glu-His-His-Lys (SEQ ID NO:8); Glu-His-His-His-Lys (SEQ ID NO:9); Glu-His-Ala-His-Lys (SEQ ID NO:10); Glu-Gly-Ala-His-Lys (SEQ ID NO:11); Glu-His-Gly-His-Gly-Lys (SEQ ID NO:12); Glu-Glu-Ala-His-Glu-Leu-Lys (SEQ ID NO:13); Glu-Glu-Ala-His-Glu-Ile-Lys (SEQ ID NO:14); Glu-Glu-Ala-His-Glu-Val-Lys (SEQ ID NO:15); Glu-Glu-Ala-His-Glu-Met-Lys (SEQ ID NO:16); Glu-Glu-Ala-His-Glu-Phe-Lys (SEQ ID NO:17); Glu-Glu-Ala-His-Glu-Tyr-Lys (SEQ ID NO:18); Glu-Glu-Ala-His-Glu-Trp-Lys (SEQ ID NO:19); Glu-Glu-Gly-Asn-Thr-Thr-Pro-Lys (SEQ ID NO:20); Glu-Glu-Gly-Asn-Glu-Thr-Glu-Pro-Lys (SEQ ID NO:21), Glu-Glu-Gly-Asn-Asp-Thr-Glu-Pro-Lys (SEQ ID NO:22); Glu-Glu-Gly-Asn-Thr-Thr-Glu-Pro-Lys (SEQ ID NO: 23); Gln-Asp-Ala-His-Lys (SEQ ID NO:24); Glu-Glu-Lys; Asp-Asp-Asp-Asp-Lys (SEQ ID NO:26); Glu-Glu-Ala-Glu-Ala-Trp-His-Trp-Leu-Lys (SEQ ID NO:29); Glu-Glu-Glu-Ala-Trp-His-Trp-Leu-Lys (SEQ ID NO:30); Leu-Asp-Gly-Arg-Leu-Glu-Ala-Leu-Lys (SEQ ID NO:31); Glu-Glu-Leu-Asp-Gly-Arg-Leu-Glu-Ala-Leu-Lys (SEQ ID NO:32); Glu-Glu-Leu-Asp-Ala-Arg-Leu-Glu-Ala-Leu-Lys (SEQ ID NO:33); Asp-Thr-His-Lys (SEQ ID NO:34); Asp-Ala-His-Lys (SEQ ID NO:35); Glu-His-His-Gly-His-Gly-Lys (SEQ ID NO:36); Asp-Ser-His-Lys (SEQ ID NO:37); Gln-Asp-Thr-His-Lys (SEQ ID NO:38); Glu-Ala-Glu-Ala-Glu-Ala-Gln-Asp-Thr-His-Lys (SEQ ID NO:39); Glu-Ala-Glu-Ala-Gln-Asp-Thr-His-Lys (SEQ ID NO:40); Glu-Ala-Gln-Asp-Thr-His-Lys (SEQ ID NO:41); Trp-His-Trp-Leu-Lys (SEQ ID NO:42); Glu-Glu-Trp-His-Trp-Leu-Lys (SEQ ID NO:43); Glu-Glu-Glu-Ala-Trp-His-Trp-Leu-Lys (SEQ ID NO:44); Glu-Glu-Ala-Glu-Lys (SEQ ID NO:45); Glu-Glu-Gly-Glu-Pro-Lys (SEQ ID NO:46); Glu-Ala-Gln-Asp-Ala-His-Lys (SEQ ID NO:47); Glu-Ala-Glu-Ala-Gln-Asp-Ala-His-Lys (SEQ ID NO:48); Glu-Ala-Glu-Ala-Glu-Ala-Gln-Asp-Ala-His-Lys (SEQ ID NO:49);

In a further embodiment, the N-terminal extension has the sequence Asp-X-His-Lys (SEQ ID NO:50) where X is Ala, Thr or Ser. The sequence Asp-X-His-Lys constitutes a heavy metal ion albumin binding site.

In a still further embodiment, the N-terminal extension has the sequence His-$Z_1$-$Z_2$-Lys (SEQ ID NO:51) wherein $Z_1$ is Glu; Asp; Asn; Gln; Ser; Thr; Gly; Leu; Ile; Val; Met; Phe or Tyr and $Z_2$ is Leu; Ile; Val; Met; Phe; Tyr; Trp or Cys. In one embodiment $Z_1$ is Glu or Asp. The sequence His-$Z_1$-$Z_2$-Lys will together with an N-terminal His residue in the desired polypeptide constitute a metal binding site homologue to Zn-binding sites in certain metalloendopeptidases such as Glu-Glu-Ala-His-Glu-Leu-Lys (SEQ ID NO:13); Glu-Glu-Ala-His-Glu-Ile-Lys (SEQ ID NO:14); Glu-Glu-Ala-His-Glu-Val-Lys (SEQ ID NO:15); Glu-Glu-Ala-His-Glu-Met-Lys (SEQ ID NO:16); Glu-Glu-Ala-His-Glu-Phe-Lys (SEQ ID NO:17); Glu-Glu-Ala-His-Glu-Tyr-Lys (SEQ ID NO:18); and Glu-Glu-Ala-His-Glu-Trp-Lys (SEQ ID NO:19).

The N-terminal extension is found to be stably attached to the precursor molecule of the invention during fermentation, protecting the N-terminal end of the precursor molecule against the proteolytic activity of yeast proteases such as Ste13p or Dap2p.

The N-terminal extension will be removed from the acylated recovered precursor molecule by means of a proteolytic enzyme which is specific for Lys. Examples of such proteolytic enzymes are trypsin or *Achromobacter lyticus* protease 1.

According to a further aspect the present invention is related to a polypeptide precursor for a desired polypeptide said polypeptide precursor having the formula N-terminal-extension-Lys-$Z_3$-$Z_4$-*polypeptide* wherein Lys is a cleavage site, the N-terminal extension has 2-14 amino acid residues as described above, $Z_3$ is the N-terminal amino acid residue in the desired polypeptide and is His or Tyr, $Z_4$ is the next amino acid residue from the N-terminal end in the desired polypeptide and is Ala, Ser or Gly, and *polypeptide* is the remaining sequence of the desired polypeptide.

In one embodiment of the present invention *polypeptide* is the relevant portion of GLP-1 or GLP-2.

Introduction of lipophilic acyl groups in naturally occurring peptides or analogues thereof has shown to lead to acylated peptides which have a protracted profile relative to the native peptide or unmodified analogues. This phenomenon is disclosed and demonstrated in WO 98/08871 which discloses acylation of GLP-1 and analogues thereof and in WO 98/08872 which discloses acylation of GLP-2 and analogues thereof. The lipophilic group may be introduced by means of mono- or dipeptide spacers as disclosed in WO 98/08871. Alternatively, the lipophilic group may be introduced by means of α-amino-α,ω-dicarboxylic acid groups as disclosed in WO 00/55119.

The present polypeptide precursor molecules will contain at least two lysine groups with a free ε-amino group, i.e. the lysine cleavage residue and at least one lysine residue in the desired polypeptide. If all lysine groups were acylated including the lysine cleavage residue, subsequent cleavage of the N-terminal extension from the desired polypeptide sequence will not be possible. Thus one of the purposes to express the desired polypeptide with an N-terminal extension is to prevent or minimize acylation of the free ε-amino group in the lysine cleavage site. The precursor molecule can then be preferentially acylated in the desired lysine residue which in the case of GLP-1 is the lysine in position 26. After acylation the acylated precursor molecule is cleaved by suitable enzymatic means as described above and the desired acylated polypeptide can be isolated.

The acylation step (iii) may be conducted at a pH between 7 and 12. In certain embodiments, the pH will be between 8 and 11.5 or between 9.0 and 10.5 and a pH value of about 9.5 to 10.5 has proven to be efficient. The temperature will be between minus 5 and 35° C. and will typically be between 0 and 20° C. or between 15 and 30° C.

In one embodiment of the present invention the acylation is conducted in the presence of divalent metal ions such as $Cu^{2+}$, $Fe^{2+}$, $Ni^{2+}$, $Co^{2+}$, $Zn^{2+}$, $Mg^{2+}$, $Mn^{2+}$ and $Ca^{2+}$. However, trivalent metal ions such as $Co^{3+}$ are also efficient for the purpose of the present invention.

According to further aspects the present invention is related to polynucleotides encoding the claimed polypeptide precursors and vectors and transformed host cells containing such polynucleotides.

DEFINITIONS

The term "preferential acylating" is meant to include and acylation process where acylation takes place at one or more preferred positions in the molecule in a substantial higher degree than at other positions in the same molecule. Thus, the acylation at the preferred positions is at least 50%, preferably at least 80% and most preferred 90-100% of the total acylation. In the present method acylation of the ε-amino group of the lysine cleavage site in the N-terminal extension should be avoided or minimized as much as possible as acylation at this position may interfere with the subsequent cleavage of the N-terminal extension from the desired end product leading to yield loss.

With "N-terminal extension" is meant a polypeptide sequence removably attached to the N-terminal amino acid residue in the desired polypeptide. The N-terminal extension may be 2-15 amino acid residues in length and will comprise a Lys residue as its C-terminal amino acid residue for cleavage from the desired polypeptide. The N-terminal extension will protect the expressed fusion polypeptide against proteolytic degradation within the host cell as described above. In addition, it is believed to prevent or minimize acylation of the ε-amino group of the lysine cleavage site in the N-terminal extension by masking said Lys residue during the acylation process.

With "desired polypeptide" is meant the ultimate polypeptide obtained after cleavage of the N-terminal extension from the precursor molecule. This expression will cover both the acylated and non-acylated version of said polypeptide. The "N-terminal extension" includes the lysine residue which constitutes the cleavage site for cleavage of the N-terminal extension from the desired polypeptide's N-terminal end. It will be understood that whenever a Lys-group is shown as the C-terminal amino acid of an N-terminal extension or a sequence being comprised in the N-terminal extension, then said Lys-residue is directly linked to the N-terminal amino acid residue of the desired polypeptide and constitutes the cleavage site. Cleavage at the Lys-residue (step iv) is preferably accomplished by means of a proteolytic enzyme which is specific Lys. Examples of such proteolytic enzymes are trypsin or *Achromobacter lyticus* protease (ALP).

An example of a desired polypeptide is GLP-1. The amino acid sequence of GLP-1 is given i.a. by Schmidt et al. (*Diabetologia* 28 704-707 (1985)). Although the interesting pharmacological properties of GLP-1(7-37) and analogues thereof have attracted much attention in recent years only little is known about the structure of these molecules. The secondary structure of GLP-1 in micelles has been described by Thorton et al. (*Biochemistry* 33 3532-3539 (1994)), but in normal solution, GLP-1 is considered a very flexible molecule.

A simple system is used to describe fragments and analogues of this peptide. Thus, for example, $Gly^8GLP-1_{(7-37)}$ designates a fragment of GLP-1 derived from $GLP-1_{(1-37)}$ by deleting the amino acid residues Nos. 1 to 6 and substituting the naturally occurring amino acid residue in position 8 (Ala) by Gly. Similarly, $Lys^{26}(N^\epsilon$-tetradecanoyl$)$-$GLP-1_{(7-37)}$ designates $GLP-1_{(7-37)}$ wherein the ε-amino group of the Lys residue in position 26 has been tetradecanoylated.

Other examples of a desired polypeptides are GLP-2 and glucagon both belonging to the GRF (growth hormone releasing factor) family of peptides having a His or Tyr in the N-terminal position and Ser, Ala or Gly in the next position, vide Adelhorst K. et al., The Journal of Biological Chemistry (1994) p 6275-6278).

"POT" is the *Schizosaccharomyces pombe* triose phosphate isomerase gene, and "TPI1" is the *S. cerevisiae* triose phosphate isomerase gene.

With "fibrillation" is meant a process where so called "fibrils" are formed. "Fibrils" is a well recognized and described phenomenon and may be composed of antiparallel β-sheets. Molecules like GLP's with little α-helical structure and a very flexible and little tertiary structure are very prone to aggregation that leads to precipitation and loss of yield if very crude chemical conditions are not taken in use such as alkaline treatment at pH ~12.

By a "leader" is meant an amino acid sequence consisting of a pre-peptide (the signal peptide) and a pro-peptide.

The term "signal peptide" is understood to mean a pre-peptide which is present as an N-terminal sequence on the precursor form of a protein. The function of the signal peptide is to allow the heterologous protein to facilitate translocation into the endoplasmic reticulum. The signal peptide is normally cleaved off in the course of this process. The signal peptide may be heterologous or homologous to the yeast organism producing the protein. A number of signal peptides may be used with the DNA construct of the invention including the YPS1 signal peptide (formally called the YAP3 signal peptide) or any functional analogue thereof (Egel-Mitani et al. (1990) YEAST 6:127-137 and U.S. Pat. No. 5,726,038) and the α-factor signal of the MFα1 gene (Thorner (1981) in *The Molecular Biology of the Yeast Saccharomyces cerevisiae*, Strathern et al., eds., pp 143-180, Cold Spring Harbor Laboratory, NY and U.S. Pat. No. 4,870,00.

The term "pro-peptide" means a polypeptide sequence whose function is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The pro-peptide may be the yeast α-factor pro-peptide, vide U.S. Pat. Nos. 4,546,082 and 4,870,008. Alternatively, the pro-peptide may be a synthetic pro-peptide, which is to say a pro-peptide not found in nature. Suitable synthetic pro-peptides are those disclosed in U.S. Pat. Nos. 5,395,922; 5,795,746; 5,162,498 and WO 98/32867. The pro-peptide will preferably contain an endopeptidase processing site at the C-terminal end, such as a Lys-Arg sequence or any functional analog thereof.

The polynucleotide sequence of the invention may be prepared synthetically by established standard methods, e.g. the phosphoamidite method described by Beaucage et al. (1981) Tetrahedron Letters 22:1859-1869, or the method described by Matthes et al. (1984) EMBO Journal 3:801-805. According to the phosphoamidite method, oligonucleotides are synthesized, for example, in an automatic DNA synthesizer, purified, duplexed and ligated to form the synthetic DNA construct. A currently preferred way of preparing the DNA construct is by polymerase chain reaction (PCR).

The polynucleotide sequence of the invention may also be of mixed genomic, cDNA, and synthetic origin. For example, a genomic or cDNA sequence encoding a leader peptide may be joined to a genomic or cDNA sequence encoding the precursor molecule of the invention, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

The invention encompasses a vector which is capable of replicating in the selected microorganism or host cell and which carries a polynucleotide sequence encoding the precursor molecule of the invention. The recombinant vector may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

In a preferred embodiment, the recombinant expression vector is capable of replicating in yeast. Examples of sequences which enable the vector to replicate in yeast are the yeast plasmid 2 μm replication genes REP 1-3 and origin of replication.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cell include amdS (acetamidase), argB (ornithine carbamoyl-transferase), pyrG (orotidine-5'-phosphate decarboxylase) and trpC (anthranilate synthase). Suitable markers for yeast host cells are ADE2, HIS3, LEU2, LYS2, MET3, TRP1, and URA3. A preferred selectable marker for yeast is the *Schizosaccharomyces pompe* TPI gene (Russell (1985) Gene 40:125-130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell.

Examples of suitable promoters for directing the transcription in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), and *Bacillus licheniformis* penicillinase gene (penP). Examples of suitable promoters for directing the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the *Saccharomyces cerevisiae* MFα1, TPI, ADHm Gal or PGK promoters.

The polynucleotide construct of the invention will also typically be operably connected to a suitable terminator. In yeast a suitable terminator is the TPI terminator (Alber et al. (1982) J. Mol. Appl. Genet. 1:419-434) or the CYC1 terminator.

The procedures used to ligate the polynucleotide sequence of the invention, the promoter and the terminator, respectively, and to insert them into a suitable vector containing the information necessary for replication in the selected host, are well known to persons skilled in the art. It will be understood that the vector may be constructed either by first preparing a DNA construct containing the entire DNA sequence encoding the precursor molecule of the invention, and subsequently inserting this fragment into a suitable expression vector, or by sequentially inserting DNA fragments containing genetic information for the individual elements followed by ligation.

The present invention also relates to recombinant host cells, comprising a polynucleotide sequence encoding the precursor molecule of the invention. A vector comprising such polynucleotide sequence is introduced into the host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The host cell may be a prokaryote or a eukaryote cell. Useful prokaryotes are bacterial cells such as gram positive bacteria including *Bacillus* and *Streptomyces* cells, or gram negative bacteria such as *E. coli* and *Pseudomonas* ssp. Cells. Eukaryote cells may be mammalian, insect, plant, or fungal cells. In a one embodiment, the host cell is a yeast cell. The yeast organism used in the process of the invention may be any suitable yeast organism which, on cultivation, produces large amounts of the precursor molecule. Examples of suitable yeast organisms are strains selected from the yeast species *Saccharomyces cerevisiae, Saccharomyces kluyveri, Schizosaccharomyces pombe, Sacchoromyces uvarum, Kluyveromyces lactis, Hansenula polymorpha, Pichia pastoris, Pichia methanolica, Pichia kluyveri, Yarrowia lipolytica, Candida sp., Candida utilis, Candida cacaoi, Geotrichum sp.,* and *Geotrichum fermentans*.

The transformation of the yeast cells may for instance be effected by protoplast formation followed by transformation in a manner known per se. The medium used to cultivate the cells may be any conventional medium suitable for growing yeast organisms. The secreted precursor of the invention may then be recovered from the medium by conventional procedures including separating the yeast cells from the medium by centrifugation, filtration or catching the precursor by an ion exchange matrix or by a reverse phase absorption matrix, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

In the present text, the designation "an analogue" is used to designate a peptide wherein one or more amino acid residues of the parent peptide have been substituted by another amino acid residue and/or wherein one or more amino acid residues of the parent peptide have been deleted and/or wherein one or more amino acid residues have been added to the parent peptide. Such addition can take place either at the N-terminal end or at the C-terminal end of the parent peptide or both.

The term "derivative" is used in the present text to designate a peptide in which one or more of the amino acid residues of the parent peptide have been chemically modified, e.g. by alkylation, acylation, ester formation or amide formation.

The amino acid residues are either indicated by the one letter or the three letter code.

EXAMPLES

Example 1

Expression of N-Terminally Extended $Arg^{34}GLP-1_{(7-37)}$

Figure 1:
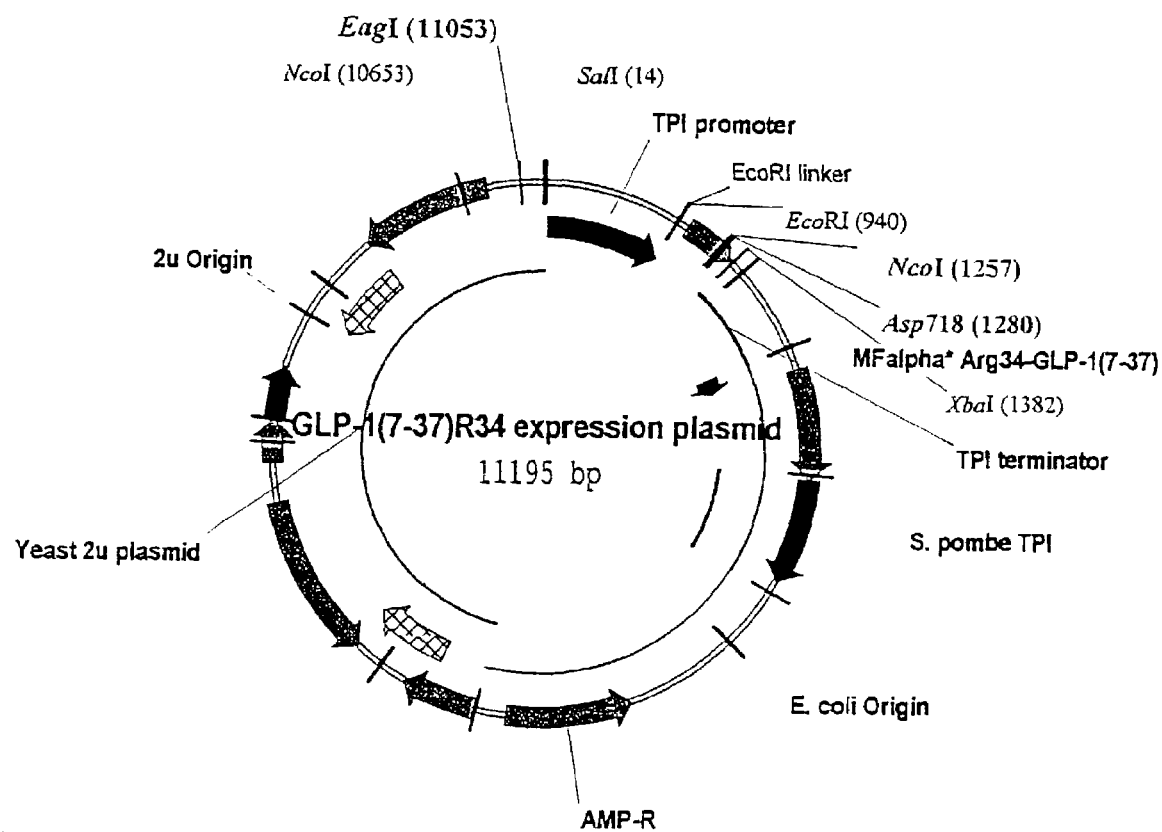
FIG. 1 shows the plasmid pKV304 which contain DNA encoding $Arg^{34}GLP-1_{(7-37)}$ under regulatory control of the TPI promoter and -terminator and the MFalpha prepro sequence. This plasmid is the starting plasmid for making expression plasmids for the precursor molecules according to the present invention.

The host strain ME1719 is a diploid strain and has a phenotype which lacks two aspartyl protease activities, i.e. YPS1 (previously called YAP3) which cleaves C-terminal side of mono- or dibasic amino acid residues (Egel-Mitani, et al., YEAST 6: 127-137, 1990) and PEP4 a vacuolar protease A responsible for activation of other proteases such as protease B, carboxypeptidase Y, aminopeptidase I, RNase, alkaline phosphatase, acid threhalase and exopolyphosphatase. Moreover the triose phosphate isomerase gene (TPI) has been disrupted which phenotype makes it possible to utilize glucose in transformants grown on glucose containing medium. The genetic background of ME1719 is MATa/αΔyps1::ura3/Δyps1::URA3 pep4-3/pep4-3Δtpi::LEU2/Δtpi::LEU2 leu2/leu2 Δura3/Δura3.

Expression plasmids containing the N-terminally extended $Arg^{34}GLP-1_{(7-37)}$ were made as follows: Plasmid pKV304 containing DNA encoding $Arg^{34}GLP-1_{(7-37)}$ without an N-terminal extension was digested with either EagI+NcoI or EagI+Asp718. After agarose electrophoresis and GeneClean™ III purification, fragments of 1.4 kb and 10 kb, respectively were isolated. Oligonucleotide adaptors corresponding to various N-terminal extensions of $Arg^{34}GLP-1_{(7-37)}$ containing NcoI and Asp718 cleavage sites were likewise purified as described above. The 1.4 kb fragment (EagI+NcoI), 10 kb fragment (EagI+Asp718) and the adaptor fragment designed for the N-terminal extension of $Arg^{34}GLP-1_{(7-37)}$ (NcoI+Asp718) were ligated and transformed in *E. coli* strain MT172 and plasmid DNA was sequenced to verify the correct N-terminally extended $Arg^{34}GLP-1_{(7-37)}$.

Plasmid DNA was then transformed into yeast strain ME1719 and yeast transformants were isolated twice on MUPD selective plates. Yeast cells were cultured in 5 ml MUPD medium for 3 days at 30° C. and culture supernatants were analyzed by HPLC and MALDI-MS (Matrix Assisted Laser Desorption/Inonisation Mass Spectrometry). MUPD medium consists of 25 g yeast extract (Bacto), 5 g $KH_2PO_4$, 1.5 g $MgSO_4 \cdot 7H_2O$, ion exchanged water to 1 liter and pH adjusted to 6.0 with 5 N $H_2SO_4$ before autoclavation at 121° C., 20 min. 30 g glucose was separately autoclaved in a 50% w/v concentration and added aseptically.

Table 1 shows the different GLP-1 precursors and the yield compared to a control with no N-terminal extension.

TABLE 1

| Extension | | Polypeptide | Yield % of control |
|---|---|---|---|
| None (control) | | $Arg^{34}GLP-1_{(737)}$ | 100 |
| EEK | | $Arg^{34}GLP-1_{(7-37)}$ | 206 |
| EEAEK | (SEQ ID NO:45) | $Arg^{34}GLP-1_{(737)}$ | 217 |
| HK | | $Arg^{34}GLP-1_{(737)}$ | 63 |
| E(EA)HK | (SEQ ID NO:1) | $Arg^{34}GLP-1_{(737)}$ | 233 |
| E(EA)$_2$HK | (SEQ ID NO:2) | $Arg^{34}GLP-1_{(737)}$ | 208 |
| E(EA)$_3$HK | (SEQ ID NO:3) | $Arg^{34}GLP-1_{(737)}$ | 223 |
| EEGHK | (SEQ ID NO:4) | $Arg^{34}GLP-1_{(7-37)}$ | 171 |
| EHPK | (SEQ ID NO:5) | $Arg^{34}GLP-1_{(7-37)}$ | 132 |
| EEGEPK | (SEQ ID NO:6) | $Arg^{34}GLP-1_{(7-37)}$ | 211 |
| EEHCK | (SEQ ID NO:7) | $Arg^{34}GLP-1_{(7-37)}$ | 58 |
| EEHHK | (SEQ ID NO:8) | $Arg^{34}GLP-1_{(7-37)}$ | 125 |
| EHHHK | (SEQ ID NO:9) | $Arg^{34}GLP-1_{(7-37)}$ | 72 |
| EHAHK | (SEQ ID NO:10) | $Arg^{34}GLP-1_{(7-37)}$ | 76 |
| EGAHK | (SEQ ID NO:11) | $Arg^{34}GLP-1_{(7-37)}$ | 97 |
| EHGHGK | (SEQ ID NO:12) | $Arg^{34}GLP-1_{(7-37)}$ | 73 |
| EEAHELK | (SEQ ID NO:13) | $Arg^{34}GLP-1_{(7-37)}$ | 220 |
| EEAHEIK | (SEQ ID NO:14) | $Arg^{34}GLP-1_{(7-37)}$ | 128 |
| EEAHEVK | (SEQ ID NO:15) | $Arg^{34}GLP-1_{(7-37)}$ | 217 |
| EEAHEMK | (SEQ ID NO:16) | $Arg^{34}GLP-1_{(7-37)}$ | 232 |
| EEAHEFK | (SEQ ID NO:17) | $Arg^{34}GLP-1_{(7-37)}$ | 226 |
| FEAHEYK | (SEQ ID NO:18) | $Arg^{34}GLP-1_{(7-37)}$ | 200 |
| EEAHEWK | (SEQ ID NO:19) | $Arg^{34}GLP-1_{(737)}$ | 200 |
| EEGNTTPK | (SEQ ID NO:20) | $Arg^{34}GLP-1_{(7-37)}$ | 216 |
| EEGNETEPK | (SEQ ID NO:21) | $Arg^{34}GLP-1_{(7-37)}$ | 145 |
| EEGNDTEPK | (SEQ ID NO:22) | $Arg^{34}GLP-1_{(7-37)}$ | 175 |
| EEGNTTEPK | (SEQ ID NO:23) | $Arg^{34}GLP-1_{(7-37)}$ | 31* |

TABLE 1-continued

| Extension | | Polypeptide | Yield % of control |
|---|---|---|---|
| QDAHK | (SEQ ID NO:24) | Arg$^{34}$GLP-1$_{(7-37)}$ | 55 |
| QDTAK | (SEQ ID NO:25) | Arg$^{34}$GLP-1$_{(7-37)}$ | 66 |
| DDDDK | (SEQ ID NO:26) | Arg$^{34}$GLP-1$_{(7-37)}$ | 190 |
| EAEAWHWLK | (SEQ ID NO:27) | Arg$^{34}$GLP-1$_{(7-37)}$ | 36 |
| EAEAEAWHWLK | (SEQ ID NO:28) | Arg$^{34}$GLP-1$_{(7-37)}$ | 34. |
| EEAEAWHWLK | (SEQ ID NO:29) | Arg$^{34}$GLP-1$_{(7-37)}$ | 20 |
| EEEAWHWLK | (SEQ ID NO:30) | Arg$^{34}$GLP-1$_{(7-37)}$ | n.d. |
| LDGRLEALK | (SEQ ID NO:31) | Arg$^{34}$GLP-1$_{(7-37)}$ | 58 |
| EELDGRLEALK | (SEQ ID NO:32) | Arg$^{34}$GLP-1$_{(7-37)}$ | 211 |
| FELDARLEALK | (SEQ ID NO:33) | Arg$^{34}$GLP-1$_{(7-37)}$ | 239 |

*Product mainly hyperglycosylated

Example 2

Acylation of EEAHK (SEQ ID NO:1)-Arg$^{34}$GLP-1$_{(7-37)}$ in the Presence and Absence of Divalent or Trivalent Metal Ions The GLP-1 analogue was produced as described in Example 1. The fermentation broth was clarified by centrifugation and 2620 ml of supernatant was diluted to 7900 ml and pH was adjusted to pH 3.1. The final conductivity was 4.9 mS/cm. A 2.6×100 cm column packed with 100 ml Pharmacia Streamline® SP Code no. 17-0993-05 was equilibrated and fluidised as recommended by the supplier (Pharmacia booklet 18-1124-26, Expanded Gel Adsorption, Principles and Methods) employing a 0.025M citrate buffer pH 3.1 and subsequently eluted by 0.5M Tris base at a flow of 0.5 ml/min. The fractions containing the GLP1 analogue was identified by analytical RP-HPLC employing a gradient of CH$_3$CN in 0.010M Tris, 0.015M Na$_2$SO$_4$ pH 7.4 with diluted H$_2$SO$_4$.

The volume of the pooled samples was 100 ml containing 361 mg of the GLP-1 analogue and the purity was 72.4%. The sample was further purified by preparative RP-HPLC. The buffer system consisted of an A-buffer 0.010M Tris, 0.015M Na$_2$SO$_4$ and 20% ethanol v/v pH 7.5 with diluted H$_2$SO$_4$ and an B-buffer consisting of 70% ethanol. Aliquots corresponding to 90 mg GLP1 analogue was applied to a HPLC column (250×20)mm packed with Nucleosil 300 Å, 7 µm, C4 obtained from Macherey-Nagel, D, equilibrated with 10% B the sample was eluted with a linear gradient from 10% B to 90% B in a total of 720 ml at a flow rate of 6 ml min. The eluent was monitored at 214 nm and 276 nm. The samples containing the GLP1 analogue were pooled, diluted with one volume of water, adjusted to pH 5.0 and cooled to 4° C. The precipitate was isolated by centrifugation and lyophilised. 286 mg was obtained and the final purity was 98.0%.

Acylation of the GLP-1 analogue was performed employing 10 mg samples of purified analogue. The sample was dissolved in 0.5 ml 0.05M Na$_2$CO$_3$ and incubated at 15° C. Glu(ONSU)N-hexadecanoyl methylester was dissolved in 0.5 ml CH$_3$CN and added to the analogue solution. Samples were taken before addition of reagent and after 15 and 30 minutes and after termination of the reaction with quenching buffer. The samples were added quenching buffer and diluted with 20% vol/vol ethanol and analysed by analytical RP-HPLC. Acylation in the presence of divalent metal ions was conducted by addition of the appropriate volume of a 0.1M solution of the metal ion before addition of the amino acid acylation reagent. The volume of Na$_2$CO$_3$ buffer was adjusted accordingly. Zn$^{2+}$ acetate was used in experiment with Zn$^{2+}$ as the metal ion.

Optimization of Acylation of EEAHK (SEQ ID NO:1)-Arg$^{34}$GLP-1$_{(7-37)}$-Lys$^{26}$γ-Glu-hexadecanoyl in the Presence of Zn$^{2+}$ Addition of more than 2 equivalents of Zn$^{2+}$ was associated by precipitation of the sample. However, the yield improved when 2 equivalents of Zn$^{2+}$ was used for acylation together with a surplus of acylation reagent. Thus, a yield of 52% was obtained together with 7% of desamidated acylation product, which is superior to 42.4% yield and 5.1% desamidated product obtained in the absence of Zn$^{2+}$.

The results are shown in Table 2 and Table 3 below.

TABLE 2

Acylation of EEAHK(SEQ ID NO:1)-Arg$^{34}$GLP-1$_{(7-37)}$ at pH 10.2, 50% CH$_3$CN by 1.3 equivalents Glu(ONSU)N-hexadecanoyl methylester

| Reaction | | 15 min | | 30 min | | 30 min stop | |
|---|---|---|---|---|---|---|---|
| GLP-1 | 0 min | GLP-1 | product | GLP-1 | product | GLP-1 | product |
| 0.0 equivalents Zn$^{2+}$ | 98.% | 36.2% | 41.4% | 35.5% | 42.4%* | 36.1% | 45.2 |
| 0.5 equivalents Zn$^{2+}$ | 98.3% | 30.2% | 42.9% | | | 32.6% | 41.7% |
| 1.0 equivalents Zn$^{2+}$ | 99.5% | 33.8% | 38 6% | | | 34.8% | 34.6% |
| 1.5 equivalents Zn$^{2+}$ | 99.3% | 30.7% | 36 3% | 29 2% | 35.5% | 31.7% | 34.2% |
| 2.0 equivalents Zn$^{2+}$ | 99.2% | 28.1% | 44 3% | 22.9% | 46.8% | 30.0% | 42.8% |
| 2.5 equivalents Zn$^{2+}$ | 99.3% | 25.0% | 39 8% | 21.3% | 46.6% | 22.5% | 45.0% |

*% 5.1% of desamidated product was obtained in this synthesis

TABLE 3

Acylation of EEAHK(SEQ ID NO:1)-Arg³⁴GLP-1$_{(7-37)}$ at pH 10.2, 50% CH$_3$CN by 2 and 3 equivalents Glu(ONSU)N-hexadecanoyl methylester and 2 equivalents Zn$^{2+}$

| Reaction | | 15 min | | 30 min | | 30 min stop | |
|---|---|---|---|---|---|---|---|
| Acylation reagent | 0 min | GLP-1 | product | GLP-1 | product | GLP-1 | product |
| 2 equivalents acylatmon reagent | 98.5% | 16 9% | 37 8% | 11.6% | 39.0% | 12 9% | 38 4% |
| 3 equivalents acylation reagent | 98.3% | 6.0% | 35.7% | 3.8% | 33.2% | | |
| 2 equivalents Zn$^{2+}$ 2 equivalents acylation reagent | 98 1 | 27 8% | 52.0% | 16 4% | 52 0%* | 19 9% | 46.1% |
| 2 equivalents Zn$^+$ 3 equivalents acylation reagent | 98 6% | 13 2% | 36.6% | 15.8% | 38.4% | 13 2% | 41 6% |

*% 7.0% of desamidated product was obtained in this synthesis.

Synthesis of Arg³⁴GLP-1$_{(7-37)}$-Lys²⁶γ-Glu-hexadecanoyl in the Presence of Zn$^{2+}$ EEAHK (SEQ ID NO:1)-Arg³⁴GLP-1$_{(7-37)}$ was acylated by addition of 2 equivalents of acylation reagent in the presence of 2 equivalents Zn$^{2+}$ for 15 min. as described above. A total of 15 µl was applied to an analytical RP-HPLC column using a TFA/CH$_3$CN/H$_2$O buffer system. The purified product corresponded to 57 µg represent a synthesis yield of 46%. The product was dried and subsequently dissolved in 0.025 ml 0.1 m NaOH at 0° C. and incubated for 20 min. After hydrolysis of the methylester, the sample was then added 15 µl 0.1 m HCl and 5 µl 0.1 m Tris.HCl and a pH indicator paper measured a pH of approximately pH 8-9. The sample was then added 10 µl CH$_3$CN and thereafter 1 µl 1 mg/ml *Achromobacter lyticus* protease I (EC 3.4.21.50) and incubated for 30 min at room temperature. A total of 10 µl was applied to the RP-HPLC system as described above and the most prominent of the 3 peaks corresponding 66.2% was further characterised and found to be identical to the desired product. The results are shown in Table 4 below.

TABLE 4

| Peak | MW calculated | MW found | Identity | Yield |
|---|---|---|---|---|
| Peak 1 | — | No signal | GLP-1 analogue | 8 5% |
| Peak 2 | 3749 29 | 3748.41 | Arg³⁴ GLP-1$_{(7-37)}$-Lys²⁶-γ-Glu-hexadecanoyl | 66 2% |
| Peak 3 | 3749.29 | 3761 8 | Unknown derivative of GLP-1 | 19 6% |

Example 3

Acylation and ALP-Processing of EEAEK (SEQ ID NO: 45)-Arg³⁴GLP-1$_{(7-37)}$

The GLP-1 precursor EEAEK (SEQ ID NO:43)-Arg³⁴GLP-1$_{(7-37)}$ was expressed in yeast as described above and recovered by adjusting the ionic strength to 7 in the fermentation supernatant and binding to a cationic column SP Sepharose Fast Flow XL (Amersham-Pharmacia). The precursor was eluted with a gradient 0-100% of 50 mM formic acid+1 M NaCl in 50 mM formic acid. After 10 column volumes the column was washed with 2 volumes of 50 mM formic acid followed by elution with 0.5 M glycine pH 9 for 3.5 column volumes. The fractions were analysed by MALDI-MS and the precursor pools were identified. These pools were applied on Reverse Phase HPLC a ZORBAX 300SB-CN column (9.4×250 mm). Elution was carried out with a gradient of 30-70% of buffer B (0.1% TFA/80% ethanol) in buffer A (0.1% TFA). Fractions were identified by UV-pattern and MALDI-MS. Pools were collected, the ethanol evaporated in vacuum and the product was lyophilised.

5 mg of lyophilised precursor EEAEK (SEQ ID NO:45)-Arg³⁴GLP-1$_{(7-37)}$ was dissolved in 350 µl water and 700 µl NMP (N-methyl-pyrrolidon-2) at room temperature and 4 equivalents of N-hexadecanoyl-l-glutamic acid-α-tert-butyl ester-γ-succinylimidyl ester was added at time zero. The pH was adjusted to 9.5 with EDIPA (ethyl di-isopropyl amin) and kept constant at 9.5 by addition of EDIPA. After 60 minutes the reaction was stopped by addition of 208 µl of a solution of 1% glycin in water. Analysis of the reaction mixture showed that 24% was unreacted product. 61% was monoacylated in position Lys²⁶. 8% was diacylated in Lys²⁶ and at the N-terminal amino group. 7% was diacylated in Lys⁶ and Lys²⁶. The mono- and diacylated molecules were converted to monoacylated Arg³⁴GLP-1$_{(1-37)}$ (69%) by processing at the lysine clevage site with ALP according to well established procedures. The result was confirmed by HPLC and MALDI-MS.

Example 4

Acylation and Cleavage of EELDARLEALK (SEQ ID NO:33)-Arg³⁴GLP-1$_{(1-37)}$, EEA-HEYK (SEQ ID NO:18)-Arg³⁴GLP-1$_{(1-37)}$ and DDDDK (SEQ ID NO: 26)-Arg³⁴GLP-1$_{(1-37)}$ The GLP-1 precursors EELDARLEALK (SEQ ID NO:33)-Arg³⁴GLP-1$_{(1-37)}$, EEAHEYK (SEQ ID NO:18)-Arg³⁴GLP-1$_{(1-37)}$ and DDDDK (SEQ ID NO: 26)-Arg³⁴GLP-1$_{(1-37)}$ were all expressed in yeast and purified as described in Example 3.

Acylation was carried out as described in Example 3. 1.3 Equivalents were used of hexadecanoyl-l-glutamic acid-α-tert-butyl ester-γ-succinylimidyl ester. HPLC and MALDI-MS analysis revealed in all cases ~15-30% unreacted substrate and around 20% diacylated product (Lys⁶, Lys²⁶) after hydrolysis with ALP directly in the acylation mixture. The results are shown in table 5.

TABLE 5

| Only monoacylated N-terminal extended Lys$^{26}$-GLP1 and diacylated N-terminal extended Lys$^6$, Lys$^{26}$-GLP1 peaks determined | | |
|---|---|---|
| Extension | % Monoacylated Lys$^{26}$ | % Diacylated Lys$^6$, Lys$^{26}$** |
| DDDDK (SEQ ID NO:26) | 80 | 20 |
| EELDARLEALK (SEQ ID NO:33) | 76 | 24 |
| EEAHEYK (SEQ ID NO:18) | 76 | 24 |

**N-terminal extended (not cleaved)

What is claimed is:

1. A method for making an acylated human GLP-1 polypeptide, said method comprising the steps of:
  (i) culturing a host cell comprising a polynucleotide sequence encoding a precursor molecule of said human GLP-1 polypeptide under suitable conditions for expression of said precursor molecule, wherein said precursor molecule comprises said human GLP-1 polypeptide and an N-terminal extension, said N-terminal extension being cleavable from the polypeptide at a lysine cleavage site;
  (ii) expressing said precursor molecule;
  (iii) separating said expressed precursor molecule from said culture;
  (iv) preferentially acylating the $\epsilon$-amino group of at least one lysine residue in said precursor molecule without acylating the $\epsilon$-amino group of the lysine residue of said lysine cleavage site, to produce an acylated precursor molecule; and
  (v) removing the N-terminal extension from said acylated precursor molecule by enzymatic cleavage to produce said acylated human GLP-1 polypeptide,
wherein said acylated human GLP-1 is $Arg^{34}GLP1_{(7-37)}$ acylated in position $Lys^{26}$.

2. The method according to claim 1, wherein said N-terminal extension is up to 15 amino acids in length.

3. The method according to claim 1, wherein said N-terminal extension is 3-15 amino acids in length.

4. The method according to claim 3, wherein said N-terminal extension is 3-8 amino acids in length.

5. The method according to claim 1, wherein one or more amino acid residues in the N-terminal extension are capable of establishing a metal ion complex binding site together with one or more amino acid residues in the N-terminal end of said human GLP-1 polypeptide.

6. The method according to claim 5, wherein said metal ion binding site is derived from:
  (i) the N-terminal end of porcine or human serum albumin;
  (ii) the Zn binding site in metalloendopeptidases; or
  (iii) a $Ca^{+2}$ binding enterokinase site from trypsinogen.

7. The method according to claim 1, wherein said N-terminal extension comprises at least one negatively charged amino acid residue that is capable of establishing a salt bridge with the lysine cleavage site N-terminal to $Arg^{34}GLP-1_{(7-37)}$.

8. The method according to claim 1, wherein $Arg^{34}GLP-1_{(7-37)}$ is sensitive to protolytic degradation at its N-terminal end and wherein said N-terminal extension prevents or minimizes such proteolytic degradation.

9. The method according to claim 1, wherein said N-terminal extension comprises at least one histidine residue.

10. The method according to claim 9, wherein one or more histidine residues in said N-terminal extension are positioned 1-4 residues from said lysine cleavage site.

11. The method according to claim 7, wherein said N-terminal extension comprises at least one Glu or Asp.

12. The method according to claim 11, wherein said Glu or Asp residues are positioned between 1 to 5 residues from said lysine cleavage site.

13. The method according to claim 11, wherein said N-terminal extension comprises a Glu-Glu-sequence.

14. The method according to claim 1, wherein said N-terminal extension comprises a sequence selected from the group consisting of: Glu-Glu-Ala-His-Lys (SEQ ID NO:1); Glu-(Glu-Ala)$_2$-His-Lys (SEQ ID NO:2); Glu-(Glu-Ala)$_3$His-Lys (SEQ ID NO:3); Glu-Glu-Gly-His-Lys (SEQ ID NO:4); Glu-His-Pro-Lys (SEQ ID NO:5); Glu-Glu-Gly-Glu-Pro-Lys (SEQ ID NO:6); Glu-Glu-His-Cys-Lys (SEQ ID NO:7); Glu-Glu-His-His-Lys (SEQ ID NO:8); Glu-His-His-His-Lys (SEQ ID NO:9); Glu-His-Ala-His-Lys (SEQ ID NO:10); Glu-Gly-Ala-His-Lys (SEQ ID NO:11); Glu-His-Gly-His-Gly-Lys (SEQ ID NO: 12); Glu-Glu-Ala-His-Glu-Leu-Lys (SEQ ID NO: 13); Glu-Glu-Ala-His-Glu-Ile-Lys (SEQ ID NO: 14); Glu-Glu-Ala-His-Glu-Val-Lys (SEQ ID NO: 15); Glu-Glu-Ala-His-Glu-Met-Lys (SEQ ID NO:16); Glu-Glu-Ala-His-Glu-Phe-Lys (SEQ ID NO:17); Glu-Glu-Ala-His-Glu-Tyr-Lys (SEQ ID NO:18); Glu-Glu-Ala-His-Glu-Trp-Lys (SEQ ID NO:19); Glu-Glu-Gly-Asn-Thr-Thr-Pro-Lys (SEQ ID NO:20); Glu-Glu-Gly-Asn-Glu-Thr-Glu-Pro-Lys (SEQ ID NO:21), Glu-Glu-Gly-Asn-Asp-Thr-Glu-Pro-Lys (SEQ ID NO:22); Glu-Glu-Gly-Asn-Thr-Thr-Glu-Pro-Lys (SEQ ID NO: 23); Gln-Asp-Ala-His-Lys (SEQ ID NO:24); Glu-Glu-Lys; Asp-Asp-Asp-Asp-Lys (SEQ ID NO:26); Glu-Glu-Ala-Glu-Ala-Trp-His-Trp-Leu-Lys (SEQ ID NO:29); Glu-Glu-Glu-Ala-Trp-His-Trp-Leu-Lys (SEQ ID NO:30); Leu-Asp-Gly-Arg-Leu-Glu-Ala-Leu-Lys (SEQ ID NO:31); Glu-Glu-Leu-Asp-Gly-Arg-Leu-Glu-Ala-Leu-Lys (SEQ ID NO:32); Glu-Glu-Leu-Asp-Ala-Arg-Leu-Glu-Ala-Leu-Lys (SEQ ID NO:33); Asp-Thr-His-Lys (SEQ ID NO:34); Asp-Ala-His-Lys (SEQ ID NO:35); Glu-His-His-Gly-His-Gly-Lys (SEQ ID NO:36); Asp-Ser-His-Lys (SEQ ID NO:37); Gln-Asp-Thr-His-Lys (SEQ ID NO:38); Glu-Ala-Glu-Ala-Glu-Ala-Gln-Asp-Thr-His-Lys (SEQ ID NO:39); Glu-Ala-Glu-Ala-Gln-Asp-Thr-His-Lys (SEQ ID NO:40); Glu-Ala-Gln-Asp-Thr-His-Lys (SEQ ID NO:41); Trp-His-Trp-Leu-Lys (SEQ ID NO:42); Glu-Glu-Trp-His-Trp-Leu-Lys (SEQ ID NO:43); Glu-Glu-Glu-Ala-Trp-His-Trp-Leu-Lys (SEQ ID NO:44); Glu-Glu-Ala-Glu-Lys (SEQ ID NO:45); Glu-Glu-Gly-Glu-Pro-Lys (SEQ ID NO:46); Glu-Ala-Gln-Asp-Ala-His-Lys (SEQ ID NO:47); Glu-Ala-Glu-Ala-Gln-Asp-Ala-His-Lys (SEQ ID NO:48); and Glu-Ala-Glu-Ala-Glu-Ala-Gln-Asp-Ala-His-Lys (SEQ ID NO:49).

15. The method according to claim 1, wherein said N-terminal extension has the formula:

$X_n$------$X_1$-Lys wherein Lys is a cleavage site and $X_n$------$X_1$ is a peptide sequence of from 2-14 amino acid residues in length having the function of preventing or minimizing acylation of the free ε-amino group in said Lys cleavage and having the further function of protecting said expressed precursor molecule from endoproteolytic cleavage, with the proviso that no X is Lys and that at least one X is His or Glu or Asp.

16. The method according to claim 15, wherein:
(i) $X_n$------$X_1$ is of 2-12 amino acid residues in length;

(ii) $X_n$------$X_1$ contains 2-8 amino acid residues which are selected from the group consisting of His; Glu; Ala; Asp; Gly; and Pro;

(iii) $X_n$------$X_1$ contains 4-10 amino acid residues which are selected from the group consisting of Glu; Asp; Ala; His; Trp; Tyr; Ile; Val; Met; and Phe; or (iv) $X_n$------$X_1$ contains 5-8 amino acid residues selected from the group consisting of Glu; Asp; Gly; Asn; Thr; Ser; and Pro.

17. The method according to claim 15, wherein said first and second amino acids from said N-terminal end of said N-terminal extension are selected from the group consisting of Glu and Asp.

18. The method according to claim 15, wherein of $X_n$------$X_1$-Lys are selected from the group consisting of Glu-Glu-Ala-His-Lys (SEQ ID NO: 1); Glu-(Glu-Ala)$_2$-His-Lys (SEQ ID NO:2); Glu-(Glu-Ala)$_3$His-Lys (SEQ ID NO:3); Glu-Glu-Gly-His-Lys (SEQ ID NO:4); Glu-His-Pro-Lys (SEQ ID NO:5); Glu-Glu-Gly-Glu-Pro-Lys (SEQ ID NO:6); Glu-Glu-His-Cys-Lys (SEQ ID NO:7); Glu-Glu-His-His-Lys (SEQ ID NO:8); Glu-His-His-His-Lys (SEQ ID NO:9); Glu-His-Ala-His-Lys (SEQ ID NO:10); Glu-Gly-Ala-His-Lys (SEQ ID NO:11); Glu-His-Gly-His-Gly-Lys (SEQ ID NO: 12); Glu-Glu-Ala-His-Glu-Leu-Lys (SEQ ID NO: 13); Glu-Glu-Ala-His-Glu-Ile-Lys (SEQ ID NO: 14); Glu-Glu-Ala-His-Glu-Val-Lys (SEQ ID NO: 15); Glu-Glu-Ala-His-Glu Met-Lys (SEQ ID NO:16); Glu-Glu-Ala-His-Glu-Phe-Lys (SEQ ID NO:17); Glu-Glu-Ala-His-Glu-Tyr-Lys (SEQ ID NO:18); Glu-Glu-Ala-His-Glu-Trp-Lys (SEQ ID NO:19); Glu-Glu-Gly-Asn-Thr-Thr-Pro-Lys (SEQ ID NO:20); Glu-Glu-Gly-Asn-Glu-Thr-Glu-Pro-Lys (SEQ ID NO:21), Glu-Glu-Gly-Asn-Asp-Thr-Glu-Pro-Lys (SEQ ID NO:22); Glu-Glu-Gly-Asn-Thr-Thr-Glu-Pro-Lys (SEQ ID NO: 23); Gln-Asp-Ala-His-Lys (SEQ ID NO:24); Glu-Glu-Lys; Asp-Asp-Asp-Asp-Lys (SEQ ID NO:26); Glu-Glu-Ala-Glu-Ala-Trp-His-Trp-Leu-Lys (SEQ ID NO:29); Glu-Glu-Glu-Ala-Trp-His-Trp-Leu-Lys (SEQ ID NO:30); Leu-Asp-Gly-Arg-Leu-Glu-Ala-Leu-Lys (SEQ ID NO:31); Glu-Glu-Leu-Asp-Gly-Arg-Leu-Glu-Ala-Leu-Lys (SEQ ID NO:32); Glu-Glu-Leu-Asp-Ala-Arg-Leu-Glu-Ala-Leu-Lys (SEQ ID NO:33); Asp-Thr-His-Lys (SEQ ID NO:34); Asp-Ala-His-Lys (SEQ ID NO:35); Glu-His-His-Gly-His-Gly-Lys (SEQ ID NO:36); Asp-Ser-His-Lys (SEQ ID NO:37); Gin-Asp-Thr-His-Lys (SEQ ID NO:38); Glu-Ala-Glu-Ala-Glu-Ala-Gln-Asp-Thr-His-Lys (SEQ ID NO:39); Glu-Ala-Glu-Ala-Gln-Asp-Thr-His-Lys (SEQ ID NO:40); Glu-Ala-Gln-Asp-Thr-His-Lys (SEQ ID NO:41); Trp-His-Trp-Leu-Lys (SEQ ID NO:42); Glu-Glu-Trp-His-Trp-Leu-Lys (SEQ ID NO:43); Glu-Glu-Glu-Ala-Trp-His-Trp-Leu-Lys (SEQ ID NO:44); Glu-Glu-Ala-Glu-Lys (SEQ ID NO:45); Glu-Glu-Gly-Glu-Pro-Lys (SEQ ID NO:46); Glu-Ala-Gln-Asp-Ala-His-Lys (SEQ ID NO:47); Glu-Ala-Glu-Ala-Gln-Asp-Ala-His-Lys (SEQ ID NO:48); and Glu-Ala-Glu-Ala-Glu-Ala-Gln-Asp-Ala-His-Lys (SEQ ID NO:49).

19. The method according to claim 6, wherein said N-terminal extension comprises the sequence His-$Z_1$-$Z_2$-Lys (SEQ ID NO:51) wherein $Z_1$ is Glu; Asp; Asn; Gln; Ser; Thr; Gly; Leu; Ile; Val; Met; Phe or Tyr and $Z_2$ is Leu; Ile; Val; Met; Phe; Tyr; Trp or Cys.

20. A method according to claim 6, wherein said N-terminal extension comprises the sequence Asp-X-His-Lys (SEQ ID NO:50) where X is Ala, Thr or Ser.

21. The method according to claim 1, wherein said enzymatic cleavage in step (iv) is achieved by use of a lysine-specific endopeptidase.

22. The method according to claim 1, wherein said yeast cell is a *Saccharomyces cerevisiae* cell.

23. The method according to claim 22, wherein said yeast cell is a ΔYPS1 cell.

24. The method according to claim 1, wherein said acylation step:
(i) is performed in an organic solvent or in a mixture of water and an organic solvent, wherein said organic solvent is $CH_3CN$ or NMP (N-methyl-pyrrolidon);
(ii) is performed in the presence of a metal ion, wherein the metal ion is selected from the group consisting of: Zn, Cu, Co, Ni, Fe, Mg, Mn or Ca;
(iii) is conducted at a pH is between 7 and 12; and
(iv) is performed at a temperature between −5° C. and 35° C.

* * * * *

UNITED STATES PATENT AND TRADEMARK OFFICE
CERTIFICATE OF CORRECTION

PATENT NO. : 7,595,172 B2
APPLICATION NO. : 10/205110
DATED : September 29, 2009
INVENTOR(S) : Jonassen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1511 days.

Signed and Sealed this

Fourteenth Day of December, 2010

David J. Kappos
*Director of the United States Patent and Trademark Office*